United States Patent [19]

Chuan et al.

[11] 3,944,834

[45] Mar. 16, 1976

[54] POLLUTION MONITOR WITH SELF-CONTAINED CALIBRATION AND CELL-BLOCK THEREFOR

[75] Inventors: Raymond L. Chuan, Altadena; Parameswar Mahadevan, Cerritos; Daryl J. Bergquist, Huntington Beach, all of Calif.

[73] Assignee: Celesco Industries Inc., Costa Mesa, Calif.

[22] Filed: Oct. 4, 1974

[21] Appl. No.: 512,338

[52] U.S. Cl............. 250/372; 250/252; 250/461 R
[51] Int. Cl.² G01D 18/00; G01J 1/42; G01N 21/38
[58] Field of Search ............ 250/461, 373, 372, 252

[56] References Cited
UNITED STATES PATENTS

| | | | |
|---|---|---|---|
| 2,974,227 | 3/1961 | Fisher et al. | 250/373 |
| 3,409,774 | 11/1968 | Dykeman | 250/252 |
| 3,795,812 | 3/1974 | Okabe | 250/373 |
| 3,854,050 | 12/1974 | Peterson et al. | 250/252 |

*Primary Examiner*—Archie R. Borchelt
*Assistant Examiner*—T. N. Grigsby
*Attorney, Agent, or Firm*—Finnegan, Henderson, Farabow and Garrett

[57] ABSTRACT

The embodiment of the pollution monitor described in the specification uses the principle of ultraviolet-induced fluorescence to detect and measure gaseous pollution in air, smokestack exhaust and other fluids. Improved calibration or standardization is effected by the use of one or more calibration cells in which a non-gaseous material simulates the fluorescence of the gaseous species under investigation, by scattering the incident ultraviolet light into a spectral region similar to that of the fluorescence of the gaseous species. Examples of suitable materials have been found to be aluminum, gold, platinum and molybdenum, all of which scatter light in the appropriate spectral region at a level which stays substantially constant with time.

In the preferred embodiment, the sample cell and the calibration cells are all formed in a single cell block by drilling holes into solid bar material which holes function as the individual cell cavities. The sample cell has ports for the flow of sample gas therethrough, while in each of the calibration cells, the metallic material is mounted to intercept and scatter the incident ultraviolet light energy. The cell block is constructed to rotate so that the several cells can be individually aligned in the light path between the ultraviolet source and fluorescence detector.

20 Claims, 3 Drawing Figures

POLLUTION MONITOR WITH SELF-CONTAINED CALIBRATION AND CELL-BLOCK THEREFOR

BACKGROUND OF THE INVENTION

The present invention relates to an ultraviolet induced fluorescence monitor for detecting the presence and quantity of pollution and more particularly to a pollution monitor of this type having an in situ calibration capability. The present invention finds particular utility in detecting accurately the concentration of gaseous pollutants, such as sulfur dioxide ($SO_2$) and nitric oxide (NO), in a sample stream or plume of ar, smoke-stack exhaust or other fluids.

As discussed in U.S. Pat. No. 3,795,812, granted Mar. 5, 1974, there are about eighty million tons of $SO_2$ released into the air each year by the burning of sulfur-containing coal and oil and the refining of oil and various metals. As explained, $SO_2$ concentrations of a few parts per million (ppm) of air can cause breathing difficulty, kill plants and hasten the deterioration of papers, leather and limestone building materials. It has therefore been proposed to limit the concentration of $SO_2$ and other stack gases to a maximum of 500 ppm.

The $SO_2$ pollution monitor described in U.S. Pat. No. 3,795,812 has a fluorescence cell into which is admitted a sample stream of air, smoke-stack gas or the like. As this sample flows through the cell, it is irradiated with ultraviolet energy in the region from about 2100 to 2300 angstroms (A) and fluoresces. This $SO_2$ fluorescence lies in the band from about 2400 A to 4200 A, and the intensity of this fluorescence is measured at right angles to the incident beam. The response of the measurement is linear over a wide range of $SO_2$ concentrations and is negligibly or only moderately affected by the presence of water vapor in the sample stream.

In the calibration of fluorescence monitors, a common technique is to flow a calibration gas of known concentration through the instrument and observe the output meter or recorder to ascertain if the instrument is reading correctly. If it is not, then the calibration controls, such as the gain and span controls associated with meters of this type, are adjusted until an accurate reading is obtained.

The problems inherent in this type of calibration is that the calibrating gas may not have the specific concentration stated because of the deterioration of gases such as $SO_2$ and NO with time. Thus, if the calibration is made to an incorrect standard, an error is incorporated into the measuring apparatus and the measurements of pollutant concentrations which follow will be inaccurate. An additional disadvantage is where it is desired to recalibrate or standardize the monitor while in the process of making measurements. This requires disconnecting the monitor from the source of sample gases which are flowing through the instrument, and connecting the source of calibration gas so that the calibration can be performed. Such calibration technique is obviously time consuming and inefficient. There is additionally the inconvenience of obtaining and transporting bottled calibration gas including the necessary valves, regulators and other plumbing which must be used.

SUMMARY OF THE INVENTION

The present invention overcomes the problems and disadvantages of the prior art by providing an ultraviolet fluorescence monitor having a self-contained calibration capability which permits calibration of the instrument to be accomplished without the need to repeat the analytical reaction with pure samples of the gaseous pollutant under investigation. Instead, one or more calibration cells are provided, each of which employs a material which simulates the fluorescence of the gaseous species under investigation; yet, unlike the pure gas samples, the fluorescent level stays substantially constant with time. The calibration cell readily replaces the sample cell in the ultraviolet light path, and calibration is simply and quickly performed.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the pollution monitor of this invention comprises a sample cell having a cell cavity, means for flowing a gas sample through the cell cavity, a first window for admitting ultraviolet energy into said cell cavity to cause fluorescence of the gaseous pollutant in said gas sample, and a second window mounted at an angle with respect to said first window for permitting fluorescent energy to emerge from said cell cavity; a calibration cell having a cell cavity, a first window for admitting ultraviolet energy into said calibration cell cavity, a second window mounted at an angle with respect to said first window of the calibration cell for permitting scattered energy to emerge from said calibration cell cavity, and a non-gaseous, scattering material mounted in the cavity of said calibration cell to intercept ultraviolet radiation entering said calibration cell and scatter said ultraviolet radiation into a spectral region which simulates the fluorescence of the gaseous pollutant, said material being positioned to project the scattered energy out of the second window of the calibration cell; means for projecting a beam of ultraviolet light toward said cells; a detector positioned to detect fluorescent or scattered energy emerging from the cells; said sample cell and said calibration cell being movably mounted with respect to said projecting means and said detector to permit selective movement of said cells into the light path between said source and detector.

Broadly, the cell block of the invention has a plurality of cells in which fluorescence can be stimulated by ultraviolet radiation and comprises a sample cell formed as a cavity in said cell block and having means for flowing a gas sample through the cell cavity, a first window for admitting ultraviolet energy into the cell cavity to cause fluorescence of the gaseous pollutant in the gas sample, and a second window mounted at an angle with respect to said first window for permitting fluorescent energy to emerge from said cell cavity; at least one calibration cell formed as a cavity in said cell block and having a first window for admitting ultraviolet energy into said calibration cell cavity, a second window mounted at an angle with respect to said first window of the calibration cell for permitting scattered energy to emerge from said calibration cell cavity, and a non-gaseous scattering material mounted in the cavity of said calibration cell to intercept ultraviolet radiation entering said calibration cell and scatter the ultraviolet energy into a spectral region which simulates the fluorescence of the gaseous pollutant, said material being positioned to project the scattered energy out of the second window of the calibration cell; means for moving said cell block to position selectively one of the cell cavities in the light path between said ultraviolet source and said detector.

The invention consists in the novel parts, constructions, arrangements, combinations and improvements shown and described. The accompanying drawings, which are incorporated in and constitute a part of this specification, illustrate one embodiment of the invention and, together with the description, serve to explain the principles of the invention.

DESCRIPTION OF THE PREFERRED EMBODIMENT

Reference will now be made in detail to the present preferred embodiment of the invention, an example of which is illustrated in the accompanying drawings.

Figure 1:
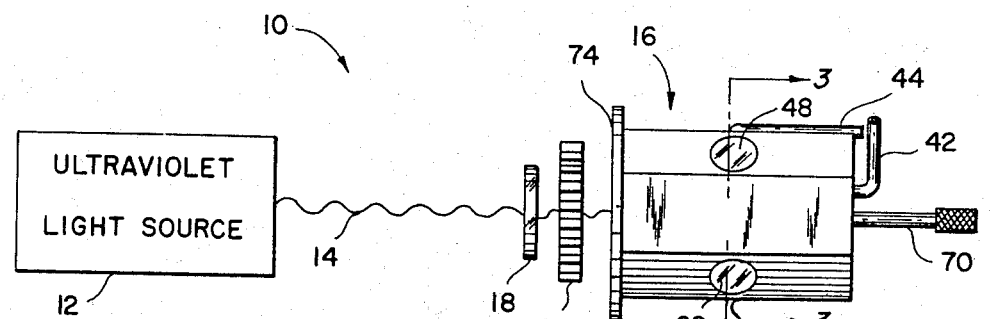
FIG. 1 is a general block and schematic diagram of a gaseous pollution monitor constructed in accordance with the present invention.

The preferred embodiment of the gaseous pollution monitor is shown in FIG. 1 and is represented generally by the numeral 10. This monitor includes means for projecting a beam of ultraviolet light. As embodied herein, this projecting means includes a source of ultraviolet light 12 which radiates ultraviolet light energy in a direction indicated by wavy line 14. Source 12 preferably radiates at one or more wavelengths in the band from about 2100A to 2300A and is optically aligned to direct its ultraviolet light energy toward a group of fluorescence cells indicated generally by numeral 16 and which will be described in greater detail later.

The ultraviolet light preferably passes through a color filter 18 which serves as a narrow bandpass filter, e.g., 2138A ± 75A, to permit only the desired band of ultraviolet energy to pass through to the fluorescence cells. A collimator 20, such as honeycomb, is shown serially arranged with filter 18 to eliminate stray light from entering the cells.

An energy or light path, including the cells 16, is formed between the light source 12 and a detector 22. Detector 22 is positioned in the monitor to detect fluorescent energy emerging from the cells. The detector 22 is depicted in this preferred arrangement as a photomultiplier tube which is energized by a suitable D.C. supply (not shown). The photo-multiplier output signal is amplified by a linear amplifier 24 and the output of the amplifier is measured by any suitable device, here indicated generally as meter 26, to give an indication of the concentration of the gaseous pollutant in the sample being monitored.

The wavelengths of the fluorescent energy which emerge from cells 16 can vary depending upon the fluid being detected. As an example, $SO_2$ fluoresces in the region from about 2400A to 4200A. Assuming that $SO_2$ is being monitored, a second color filter 28 is preferably positioned at the output of cells 16 to permit only a desired band, e.g., 4000A ± 100A, of radiant energy to pass to detector 22. A second collimator 30 is serially arranged with filter 28 to eliminate stray light from contacting the detector 22.

For a more complete description of the construction of the above-described component parts of a fluorescence monitor and the manner in which this monitor is operated to detect gaseous pollutants and measure the concentration thereof, attention is invited to the aforementioned U.S. Pat. No. 3,795,812 which is hereby specifically incorporated by reference.

Figure 2:
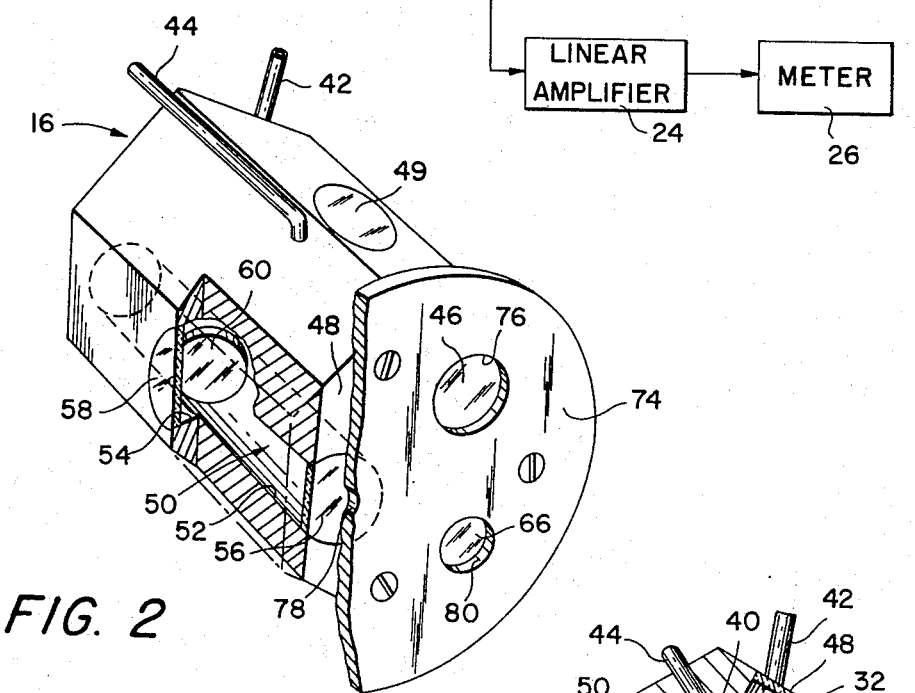
FIG. 2 is a perspective view of the preferred embodiment of the cell block in partial cut-away form to reveal details of its construction.
Figure 3:
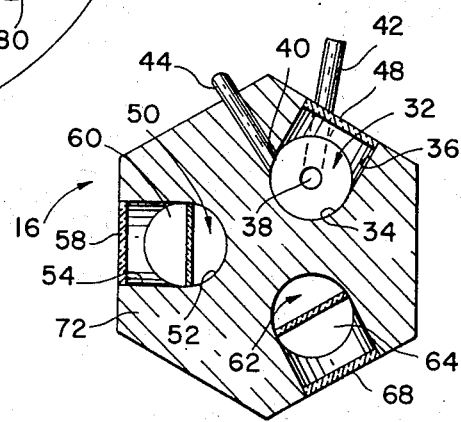
FIG. 3 is a sectional view of the preferred embodiment of the cell block taken along line 3—3 of FIG. 1.

With additional reference now to FIGS. 2 and 3, there is shown, respectively, perspective and cross-sectional views of the preferred embodiment of a movable cell block 16 constructed in accordance with the teachings of the present invention. This cell block has a plurality of cells in which fluorescence can be stimulated by ultraviolet radiation, and is designed to be mounted in a pollution monitor between the source of ultraviolet radiation and the fluorescence detector.

Referring first to the fluorescence cells generally, and in accordance with the present invention, a sample cell is provided having a cell cavity and means for flowing a gas sample through a cell cavity. As embodied herein, the sample cell comprises a cavity 32 formed in elongated cell block 16. Cavity 32 includes a first hole 34 suitably formed in the cell block 16 from its front face inwardly and parallel to its longitudinal axis, and a second hole 36 extending inwardly from the side of the cell block at substantially a right angle to hole 34 so that the two holes 34 and 36 intersect in substantially the manner shown.

As here embodied, the flowing means includes an intake aperture 38 for admitting a gas sample into the sample cell cavity 32 and an exhaust aperture 40 for exhausting the gas sample from the sample cell cavity. Preferably, an intake tube 42 is connected from a gas sample source (not shown) to intake aperture 38, and similarly an exhaust tube 44 is connected to the exhaust aperture to transport the gas sample away out of the cell block. The apertures 38 and 40 can be conveniently formed by drilling holes through the aft end face and side of cell block 16 into the cavity 32 of the sample cell.

In accordance with the invention, the sample cell has a first window for admitting ultraviolet energy into said cell cavity to cause fluorescence of the gaseous pollutant in said gas sample. As embodied herein, the first window 46 of the sample cell is mounted in hole 34 at the front end face 48 of the cell block. The first window 46, which can be termed the incident window, is preferably made of a material such as quartz which will pass the incident ultraviolet energy into cavity 32. Window 46 can be held in place by any suitable means such as cement which preferably also serves to seal hole 34.

In accordance with the invention, the sample cell further includes a second window 49 mounted at an angle with respect to said first window 46 for permitting fluorescence energy to emerge from the cell cavity 32. As embodied herein, the second window 49 is mounted in hole 36 at the side of the cell block 16. Again, this window is made of quartz or other suitable material which can pass fluorescent energy from the cell cavity 32, and can be retained by cement which also acts as a seal for hole 36. Because the holes 34 and 36 are preferably formed perpendicular to each other, the windows 46 and 49 are mounted at approximately 90° with respect to each other.

In accordance with the present invention, there is also provided at least one calibration cell, said cell having a cell cavity. As here embodied, the calibration cell comprises a cavity 50 formed in the elongated cell block 16. Cavity 50 includes a hole 52 suitably formed in the cell block 16 parallel to its longitudinal axis and thus parallel to hole 34 of sample cell 32. Also forming cavity 50 is a second hole 54 which extends inwardly from the side of cell block 16 at substantially a right angle to hole 52 so that the two holes 52 and 54 intersect in substantially the manner shown.

In accordance with the invention, the calibration cell has a first window for admitting ultraviolet energy into the cavity of the calibration cell. As here embodied, the first window 56 of calibration cell cavity 50 is mounted in hole 52 at its opening in end face 48. This first window 56, which can be termed the incident window, is preferably made of a material such as quartz which passes the incident ultraviolet energy into cavity 50. Window 56 can be held in place by any suitable means such as cement.

In accordance with the invention, the calibration cell also includes a second window which is mounted at an angle with respect to the first window of the calibration cell for permitting scattered energy to emerge from the calibration cell cavity. As here embodied, the second window 58 of the calibration cell is mounted in hole 54 at the side of cell block 16. Again, this window is made of quartz or other suitable material which can pass light energy out of the calibration cell 50. Window 58 can be retained in place by cement or other suitable means. Because holes 52 and 54 are preferably formed perpendicular to each other, the windows 56 and 58 are mounted at approximately 90° with respect to each other.

In accordance with the invention, the calibration cell has a non-gaseous material mounted in its cavity to intercept ultraviolet radiation entering the calibration cell and scatter said ultraviolet radiation into a spectral region which simulates the fluorescence of the gaseous pollutant, said material being positioned to project the scattered energy out of the second window of the calibration cell. As here embodied, this material is shaped as a disc or plate 60 which is positioned in the calibration cell cavity 50 at the intersection of the two holes 52 and 54. Plate 60 intercepts the ultraviolet light energy entering hole 52 via window 56, and the material of the plate scatters the incident energy. This plate is preferably mounted at approximately 45° with respect to the first and second windows 56 and 58 of the calibration cell 50. When the plate material scatters the ultraviolet light, scattered light is emitted out through hole 54 and window 58. Preferably, the scattering material is selected so as to simulate the fluorescence of the gas under investigation in the sample cell 32, the purpose being to generate a signal for the detector which is essentially equivalent to the signal being generated in the sample cell.

Many non-gaseous materials will simulate fluorescence when irradiated with ultraviolet energy. As an example, in the analysis of $SO_2$, a polished aluminum reflector has been found to simulate closely the fluorescence of $SO_2$ and can be used as the material for plate 60 in the calibration cell 50. Other examples of materials which have been found suitable include gold, platinum, and molybdenum. These materials generally scatter light energy over a wide band of wavelengths which preferably includes the band of the gaseous pollutant being monitored. The narrow band of interest is readily selected by filter 30 so that only this desired band is passed on to detector 22. A particular advantage of these metallic, scattering materials is that the simulated fluorescent energy level remains substantially constant with the passage of time.

More than one calibration cell can be used. In the preferred embodiment, an additional calibration cell 62, identical in construction to the aforedescribed calibration cell 50, is shown. Cell 62 includes a disc or plate 64 made of a non-gaseous, scattering material which is mounted in the cell cavity to intercept incident ultraviolet energy admitted through window 66 and to scatter energy out of the cell 62 through window 68.

In the formation of the cell cavities in cell block 16, the intersecting holes are preferably made by drilling into the front face 48 and the side of the cell block. The elongated holes such as hole 52 which extend inwardly from the front end face terminate short of the aft end face of the cell block. The cell block can be conveniently formed of solid bar stock aluminum or steel 72. After the holes have been drilled, the interior of these holes is coated with a material which seals the metal so that it will not react with the sample gas and which prevents the metal from scattering light when irradiated by ultraviolet energy. A suitable coating material has been found to be Teflon.

While it is not necessary that the cell cavities be formed in block 16 insofar as the overall construction of the pollution monitor is concerned, this is nevertheless the preferred construction. One advantage of such construction is the rigid, fixed positioning of the several cells with respect to each other which helps to ensure optical alignment of the cells as they are selectively moved into the path of the ultraviolet light.

The cell block 16 is initially mounted in the pollution monitor so that the incident window of one of the cells is optically aligned with the ultraviolet light source, and the exit window of the same cell is optically aligned with the detector 22. In accordance with the invention, there are means provided for moving the cell block to position selectively one of the cell cavities in the light path between the ultraviolet source and the detector. As here embodied, this moving means includes a shaft 70 attached to the cell block 16 which permits rotation of this cell block about its longitudinal axis. Preferably, shaft 70 is manually rotated. As cell block 16 is revolved, the cells 32, 50 and 62 are individually positioned in the light path of the ultraviolet source and detector.

As can best be seen in FIG. 3, if cell block 16 is initially mounted in the pollution monitor so that sample cell 32 is in optical alignment with the source 12 and detector 22, rotation of the cell block approximately 120° clockwise (when facing front end face 48) places calibration cell 50 in alignment with the ultraviolet source and detector. Alternatively, rotation 120° counter-clockwise brings calibration cel 62 into alignment. Tubes 42 and 44 which are connected into sample cell 32 can be made sufficiently flexible to permit this rotation.

The purpose of having more than one calibration cell is to provide several calibration ranges to match the wide range of gas concentrations which can be encountered. As an example, one calibration cell can be selected to simulate fluorescence in a low range of $SO_2$ concentrations, e.g., 0–500 ppm, and the other calibration cell can be selected to simulate a high range of $SO_2$ concentrations, e.g., 0–5,000 ppm. Thus, depending upon the concentration of $SO_2$ in the sample gas which is being monitored, either calibration cell 50 or 62 is used to calibrate or standardize the system.

In order to obtain these several ranges of calibration, there are means provided for controlling the amount of ultraviolet energy admitted into the several cells. This controlling means preferably includes a plate 74 positioned on the front end face 48 of the cell block 16 over the incident windows of the cells. This plate can be retained by any suitable means such as the set screws shown.

Apertures or holes of different sizes are formed in plate 74 and are aligned with the incident windows of the cell cavities to permit a controlled amount of ultraviolet light into each cell cavity. As depicted in FIG. 2, hole 76 of plate 74 is aligned with incident window 46 of the sample cell 32; hole 78 is aligned with incident window 56 of calibration cell 50; and hole 80 is aligned with incident window 66 of the other calibration cell 62.

The size of hole 76 is predetermined to ensure that sufficient ultraviolet light energy is admitted into the sample cell 32 to cause optimum fluorescence of the sample gas which is admitted into the cell during operation. The size of hole 78 and 80 are determined by such factors as the material used on scattering plates 60 and 64 and the energy level of source 12 so that the scattering which occurs in these two calibration cells simulates the fluorescence of the sample gas within the two calibration ranges discussed above. For example, hole 78 is smaller than hole 80 and thus calibration cell 50 functions in the low range of 0–500 ppm. Hole 80 is sized to permit operation of cell 62 in the calibration range of 0–5,000 ppm. Obviously, other calibration ranges could be used and the size of the holes in plate 74 would vary.

In the description of operation it will be assumed that a smoke stack is being monitored to determine if $SO_2$ is present in the stack gases and if so the concentration of $SO_2$ in these gases. Intake tube 42 is connected by means of a flexible inert tubing (not shown) to the smoke stack to carry a sample of the stack gases to the sample cell 32. Exhaust tube 44 carries away the sample gases after passage through the sample cell. A pump (not shown) may be connected to either the intake or exhaust tube to ensure that a continuous sample stream of the stack gases flows through the sample cell 32.

Cell block 16 is positioned so that the incident window 46 is optically aligned with the ultraviolet light source 12. Ultraviolet light energy emanated by source 12 is filtered at 18 and passes through window 46 into the cavity of sample cell 32. If $SO_2$ is present in the sample stream, this $SO_2$ fluoresces in the region from about 2400 A to 4200 A, and a portion of this fluorescence, emerging at right angles to beam, incident beam passes through window 48. Filter 28 passes the fluorescent energy within the band pass of the filter, and this energy impinges upon the photomultiplier tube 22. The output of the photomultiplier tube is amplified by linear amplifier 24 and then measured at meter 26.

Although the pollution monitor shown is preferably calibrated at the start of the monitoring operation, changes in the system can occur during monitoring which cause errors to appear in the output measurement. These errors can be caused by such things as changes in the intensity of the ultraviolet light source and in the sensitivity of the detector 22, as well as by drift in the amplifier 24 and other electronics. The present invention permits in situ calibration or standardization of the pollution monitor while monitoring is taking place without the need to disconnect the source of the gas sample. Because the same source, filters, and detecting and measuring apparatus are used while monitoring the stack gases and during calibration, the performance of the complete system is assessed during calibration and can be corrected as necessary so that the accuracy of the monitoring is preserved.

Assuming that $SO_2$ concentrations in the range of 0–500 ppm are being measured at meter 26, cell block 16 is rotated clockwise until calibration cell 50 is brought into optical alignment with source 12 and detector 22. Ultraviolet energy passes through filter 18, hole 78 in plate 74, and incident window 56 into the cavity of this calibration cell. This energy strikes the metal scatterer 60 and is scattered over a wide band. Because the scatterer 60 is mounted at 45° to the incident beam, scattered energy is directed through hole 54 and window 58, through filter 30 to detector 22. Calibration cell 50 is designed to give a predetermined reading, e.g., 250 ppm, and meter 26 is observed to see if this reading is obtained. Should this reading not be obtained, the system is adjusted, as for example by adjusting the conventional gain and span controls of the amplifier 24, in order to correct the reading of meter 26 to the known standard. Once this has been accomplished, then cell block 60 is immediately rotated counter-clockwise to bring sample cell 32 back into alignment with light source 12. Measurement of $SO_2$ concentrations resumes.

In the foregoing description of operation, the concentration of $SO_2$ in the sample was stated to lie in the range of 0–500 ppm. Had the range been 0–5,000 ppm, calibration or standardization would have been obtained by rotation of cell block 16 counter-clockwise to place calibration cell 62 in alignment with light source 12. In such event, metallic plate 64 simulates the $SO_2$ fluorescence of the sample cell and the scattered light energy which passes out through window 68 to detector 22 permits calibration of the pollution monitor with reference to the standard of cell 62.

It will be apparent to those skilled in the art that various modifications and variations can be made in the pollution monitor of the present invention and in the construction of the cell block 16 without departing from the scope or spirit of the invention. As an example, there can be more than one cover plate 74 provided each having a different selection of aperture sizes which permit monitoring and calibration over additional concentration ranges. Thus, it is intended that the present invention cover the modifications and variations of this invention provided they come within the scope of the appended claims and their equivalents.

What is claimed is:

1. A pollution monitor for detecting the presence of a gaseous pollutant in a gas sample comprising:
   A. A sample cell having:
      1. a cell cavity,
      2. means for flowing a gas sample through the cell cavity, 3. a first window for admitting ultraviolet energy into said cell cavity to cause fluorescence of the gaseous pollutant in said gas sample, and
4. a second window mounted at an angle with respect to said first window for permitting fluorescent energy to emerge from said cell cavity;

B. A calibration cell having:
1. a cell cavity,
2. a first window for admitting ultraviolet energy into said calibration cell cavity,
3. a second window mounted at an angle with respect to said first window of the calibration cell for permitting scattered energy to emerge from said calibration cell cavity, and
4. a non-gaseous, scattering material mounted in the cavity of said calibration cell to intercept ultraviolet radiation entering said calibration cell and scatter said ultraviolet energy into a spectral region which simulates the fluorescence of the gaseous pollutant, said material being positioned to project the scattered energy out of the second window of the calibration cell;

C. Means for projecting a beam of ultraviolet light toward said cells;
D. A detector positioned to detect fluorescent or scattered energy emerging from said cells;
E. Said sample cell and said calibration cell being movably mounted with respect to said projecting means and said detector to permit selective movement of said cells into the light path between said source and detector.

2. A pollution monitor as claimed in claim 1 further comprising:
A. means for moving said cells to position selectively one of the cell cavities in the light path between said projecting means and said detector so that ultraviolet energy can selectively enter said cavities to cause fluorescence therein.

3. A pollution monitor as claimed in claim 2 wherein:
A. the first window in each cell is mounted at approximately 90° with respect to the second window of its associated cell.

4. A monitor as claimed in claim 3 wherein:
A. said scattering material is mounted in the cavity of said calibration cell at approximately 45° with respect to said first and second windows of said calibration cell.

5. A pollution monitor as claimed in claim 4 wherein said flowing means includes:
A. an intake aperture for admitting a gas sample into the cavity of the sample cell, and
B. an exhaust aperture for exhausting the gas sample from the cavity of the sample cell.

6. A monitor as claimed in claim 5 further comprising:
A. a second calibration cell constructed in the same manner as said calibration cell, and
B. means for controlling the amount of ultraviolet energy admitted into all of said cells.

7. A monitor as claimed in claim 6 wherein:
A. said cells are formed in an elongated cell block in which the cavities comprise holes formed in the cell block, said cell block having:
1. an end face in which the first cell windows are mounted:
2. a side in which the second cell windows are mounted; and
B. said controlling means comprises:
1. a plate positioned on the end face of the cell block over the first windows of the cells; and
2. apertures of varying sizes formed in the plate and aligned with said first windows to permit a controlled amount of ultraviolet light into each cavity.

8. A monitor as claimed in claim 7 wherein:
A. said moving means includes a shaft attached to said cell block to permit rotation of said cell block to selectively position said cavities in said light path.

9. A monitor as claimed in claim 8 wherein:
A. said projecting means includes a source of ultraviolet energy.

10. A monitor as claimed in claim 9 wherein:
A. said scattering material is selected from the group consisting of aluminum, gold, platinum and molybdenum.

11. A pollution monitor as claimed in claim 1 wherein:
A. said sample cell and said calibration cell are formed as separate cavities in a cell block;
B. means for moving said cell block to position selectively one of said cavities in the light path between said projecting means and said detector.

12. A pollution monitor as claimed in claim 11 wherein:
A. said moving means includes a shaft attached to the cell block to permit rotation of said cell block.

13. A movable cell block having a plurality of cells in which fluorescence can be stimulated by ultraviolet radiation, and designed to be mounted in a pollution monitor between a source of ultraviolet radiation and a fluorescence detector and comprising:
A. a sample cell formed as a cavity in said cell block and having:
1. means for flowing a gas sample through the cell cavity,
2. a first window for admitting ultraviolet energy into the cell cavity to cause fluorescence of the gaseous pollutant in the gas sample, and
3. a second window mounted at an angle with respect to said first window for permitting fluorescent energy to emerge from said cell cavity;
B. at least one calibration cell formed as a cavity in said cell block and having:
1. a first window for admitting ultraviolet energy into said calibration cell cavity,
2. a second window mounted at an angle with respect to said first window of the calibration cell for permitting scattered energy to emerge from said calibration cell cavity, and
3. a non-gaseous, scattering material mounted in the cavity of said calibration cell to intercept ultraviolet radiation entering said calibration cell and scatter the ultraviolet energy into a spectral region which simulates the fluorescence of the gaseous pollutant, said material being positioned to project the scattered energy out of the second window of the calibration cell;
C. means for moving said cell block to position selectively one of the cell cavities in the light path between said ultraviolet source and said detector.

14. A cell block as claimed in claim 13 wherein:
A. the first window in each cell is mounted at approximately 90° with respect to the second window of its associated cell.

15. A cell block as claimed in claim 14 wherein:

A. said scattering material is mounted in the cavity of said calibration cell at approximately 45° with respect to said first and second windows of said calibration cell.

16. A cell block as claimed in claim 15 further comprising:
   A. a second calibration cell constructed in the same manner as said calibration cell, and
   B. means for controlling the amount of ultraviolet energy admitted into all of said cells.

17. A cell block as claimed in claim 16 further comprising:
   A. an end face in which the first cell windows are mounted;
   B. a side in which the second cell windows are mounted;
   C. said cell cavities being formed by drilling holes into the end face and side of the cell block; and
   D. said controlling means comprises:
      1. a plate positioned on the end face of the cell block over the first windows of the cells; and
      2. apertures of varying sizes formed in the plate and aligned with said first windows to permit a controlled amount of ultraviolet light into each cavity.

18. A pollution monitor as claimed in claim 17 wherein said flowing means includes:
   A. an intake aperture for admitting a gas sample into the cavity of the sample cell, and
   B. an exhaust aperture for exhausting the gas sample from the cavity of the sample cell.

19. A cell block as claimed in claim 18 wherein:
   A. said moving means includes a shaft attached to said cell block to permit rotation of said cell block to selectively position said cavities in said light path.

20. A cell block as claimed in claim 19 wherein:
   A. said scattering material is selected from the group consisting of aluminum, gold, platinum and molybdenum.

* * * * *